United States Patent
Song et al.

(10) Patent No.: US 8,436,188 B2
(45) Date of Patent: May 7, 2013

(54) METHOD FOR THE SEPARATION OF S-(−)-AMLODIPINE FROM RACEMIC AMLODIPINE

(75) Inventors: Seog Beom Song, Gyeonggi-do (KR); Il Hwan Cho, Seoul (KR); Yong Sik Youn, Gyeonggi-do (KR); Dong Kwon Lim, Gyeonggi-do (KR)

(73) Assignee: CJ Cheiljedang Corporation (KR)

(*) Notice: Subject to any disclaimer, the term of this patent is extended or adjusted under 35 U.S.C. 154(b) by 746 days.

(21) Appl. No.: 12/447,306

(22) PCT Filed: Oct. 26, 2007

(86) PCT No.: PCT/KR2007/005330
§ 371 (c)(1),
(2), (4) Date: Apr. 27, 2009

(87) PCT Pub. No.: WO2008/051056
PCT Pub. Date: May 2, 2008

(65) Prior Publication Data
US 2010/0069445 A1    Mar. 18, 2010

(30) Foreign Application Priority Data
Oct. 27, 2006 (KR) .................. 10-2006-0105107

(51) Int. Cl.
*C07D 211/26* (2006.01)
*C07D 211/28* (2006.01)
*C07D 213/80* (2006.01)
*C07D 213/803* (2006.01)
*A61K 31/44* (2006.01)

(52) U.S. Cl.
USPC .................. 546/321; 546/231; 514/356

(58) Field of Classification Search .......... C07D 211/26, 211/28, 213/80, C07D 213/803; A61K 31/44
See application file for complete search history.

(56) References Cited

U.S. PATENT DOCUMENTS

| 5,750,707 A | * | 5/1998 | Spargo ............ 546/321 |
| 6,046,338 A | | 4/2000 | Spargo |
| 6,057,344 A | | 5/2000 | Young |
| 6,080,761 A | | 6/2000 | Chahwala et al. |
| 6,291,490 B1 | | 9/2001 | Young |
| 6,646,131 B2 | | 11/2003 | Zhang |
| 6,822,099 B2 | * | 11/2004 | Senanayake et al. ........ 546/315 |

FOREIGN PATENT DOCUMENTS

| EP | 0331315 A2 | 9/1989 |
| JP | H07501547 | 2/1995 |
| KR | 20040023160 A | 3/2004 |
| WO | 9310779 A1 | 6/1993 |
| WO | 9525722 A1 | 9/1995 |
| WO | 03035623 A1 | 5/2003 |
| WO | WO 03/035623 A1 * | 5/2003 |
| WO | WO 03035623 A1 * | 5/2003 |
| WO | 2004024689 A1 | 3/2004 |
| WO | WO 2004024689 A1 * | 3/2004 |
| WO | 2006043148 B1 | 6/2006 |
| WO | 2006059886 A1 | 6/2006 |

OTHER PUBLICATIONS

Goldmann et al., J. Med. Chem 35; 3341-3344 (1992).
Arrowsmith et al., J. Med. Chem., 29; 1696-1702 (1986).
International Search Report, PCT/KR2007/005330, dated Feb. 4, 2008.

* cited by examiner

*Primary Examiner* — Janet Andres
*Assistant Examiner* — Ben Michelson
(74) *Attorney, Agent, or Firm* — Lerner, David, Littenberg, Krumholz & Mentlik, LLP

(57) ABSTRACT

Disclosed is a method for the separation of S-(−)-amlodipine from a racemic amlodipine. Featuring the use of inexpensive L-tartaric acid as an optical resolution agent and DMAC as a solvent, the separation method allows the resolution of S-(−)-amlodipine from racemic amlodipine at high yield and to a satisfactory enantiomeric excess and thus is economically favorable and applicable to the mass production of the optical isomer.

6 Claims, No Drawings

METHOD FOR THE SEPARATION OF S-(−)-AMLODIPINE FROM RACEMIC AMLODIPINE

TECHNICAL FIELD

The present invention relates to a method for the separation of S-(−)-amlodipine from a racemic amlodipine.

BACKGROUND ART

Amlodipine, the IUPAC Name for 3-ethyl-5-methyl-2-(2-aminoethoxymethyl)-4-(2-chlorophenyl)-1,4-dihydro-6-methyl-3,5-pyridinedicarboxylate, is a long-acting calcium channel blocker useful in the treatment of cardiovascular diseases, such as angina pectoris, hypertension, congestive heart failure, etc.

Amlodipine is a chiral compound with a chiral center. In general, pure stereoisomers are known to have better therapeutic effects than racemic mixtures. Furthermore, racemic compounds tend to have different pharmacokinetic profiles, depending on the steric arrangement of the isomer compounds or their salts. There are two possible stereoisomers of amlodipine because it has one chiral center, that is, R-(+)-amlodipine and (S-(−)-amlodipine, which are different from each other in pharmacokinetic profile. The R-(+)-isomer of amlodipine is a potent inhibitor of smooth muscle cell migration despite the fact that it does not exhibit calcium channel-blocking activity (U.S. Pat. No. 6,080,761). So, it is useful for preventing and treating atherosclerosis. On the other hand, the (S)-(−)-isomer of amlodipine is a potent calcium channel blocker. For ideal use as a calcium channel blocker, amlodipine is administered in the form of S-(−)-amlodipine, substantially free of its (+) stereoisomer (U.S. Pat. No. 6,057,344). U.S. Pat. No. 6,291,490 also discloses S-(−)-amlodipine, reporting that S-(−)-amlodipine avoids the adverse effect of amlodipine in racemic mixtures. Therefore, there is a need for a methodology by which chiral compounds such as amlodipine are separated as pure isomers.

Several methods of separating optical amlodipine isomers are known: 1) Resolution of two optical amlodipine isomers by the separation of the resolution of diastereomeric azide ester (represented by the following Formula 1(a)) (J. E. Arrowsmith et al., J. Med. Chem. (1986), 29, 1696], 2) Separation of an intermediate (represented by the following Formula 1(b)) by use of cinchonidine carboxylate (EP 0,331, 315), and 3) Chromatographic separation of diastereomeric amide ester (represented by the following Formula 1(c)) (S. Goldman et al., J. Med. Chem. (1992) 35 3341). However, it was noted that these methods are not suitable for industrial application.

[Formula 1]

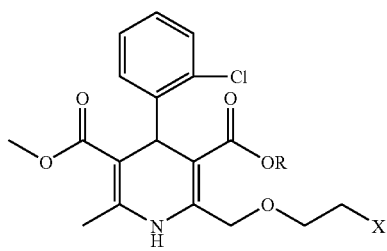

(a) R=CH$_2$CH(OCH$_3$)Ph, X=N$_3$,
(b) R=H, X=N$_3$,
(c) R=CH$_2$CH$_3$, X=(1S)-camphanoyl amine.

Recently, a series of techniques having improved industrial applicability has been reported. Most of the techniques feature the formation of diastereomeric salts of amlodipine with D- or L-tartaric acid and subsequent separation with an appropriate solvent. These techniques may be useful because diastereomeric salts of amlodipine can be separated merely by a physical process, and the salts may also be easily detached with a base.

For example, U.S. Pat. No. 6,046,338 and Korean Patent No. 10-0188980 disclose the separation method of enantiomeric isomers of amlodipine from mixtures thereof by reacting the mixture of isomers with either L- or D-tartaric acid in dimethyl sulfoxide (DMSO) for the precipitation of DMSO solvate of D- or L-tartrate. The precipitate is a amlodipine-hemitartrate-DMSO monosolvate composed of 2:1:2 amlodipine:tartrate:DMSO.

U.S. Pat. No. 6,646,131 described a method for the separation of (R)-(+)- and (S)-(−)-isomers of amlodipine through the reaction of the mixture of isomers with D- or L-tartaric acid in deuterium-substituted dimethyl sulfoxide (DMSO-d$_6$)) for the precipitation of a DMSO-d$_6$ solvate of a D- or L-tartrate salt of amlodipine isomers.

Korean Patent Publication No. 10-2004-62575 discloses the separation of optical isomers of amlodipine via the formation of amlodipine-hemitartrate-DMAC monosolvate in dimethylacetate amide (DMAC) and treatment with a base.

However, as described in the patent document, D- and L-tartaric acid are used as optical resolution agents for forming S-(−)- and R-(+)-amlodipine, respectively. Particularly, the methods disclosed in U.S. Pat. No. 6,046,338 and Korean Patent No. 10-0188980 are advantageous in terms of the high yield and optical purity of amlodipine enantiomers, but are disadvantageous in terms of economy because D-tartaric acid, serving as an optical resolution agent for separating S-(−)-amlodipine, is expensive. Further, the methods are not readily applicable to industrial scale production because the solvent DMSO is used.

With the aim of overcoming the problems encountered in the prior art, Korean Patent No. 10-0476636 suggests a method for the resolution of S-(−)-amlodipine with L-(+)-tartaric acid. Although having an advantage over the previously mentioned patents in terms of economy, it is not suitable for application to mass production due to the use of DMSO.

Leading to the present invention, intensive and thorough research into the industrially applicable resolution of optical isomers of amlodipine, conducted by the present inventors, resulted in the finding that the use of L-(+)-tartaric acid as an optical resolution agent, with dimethylacetamide (DMAC) serving as a solvent, allows S-(−)-amlodipine to be resolved from the racemic mixture thereof at a high yield and to a satisfactory enantiomeric excess.

DISCLOSURE OF INVENTION

Technical Problem

It is an object of the present invention to provide a method for the separation of S-(−)-amlodipine from a racemic mixture, which is applicable on an industrial scale, featuring the use of L-tartaric acid and dimethylacetamide (DMAC).

Technical Solution

In order to accomplish the above object, the present invention provides a method for the separation of S-(−)-amlodipine from a racemic mixture, comprising:

1) reacting an amlodipine racemate with L-tartaric acid in a dimethylacetamide (DMAC) solvent and filtering off a precipitate of R-(+)-amlodipine-hemi-L-tartrate-DMAC solvate, 2) adding methylene chloride and n-hexane to the remaining filtrate of step 1) to afford an S-(−)-amlodipine-hemi-L-tartrate-DMAC solvate, and 3) purifying the S-(−)-amlodipine-hemi-L-tartrate-DMAC solvate with methanol, followed by base treatment.

Hereinafter, a detailed description will be given of the present invention.

Featuring the use of L-tartaric acid and DMAC, the separation method of the present invention takes advantage of the difference in DMAC solubility between R-(+)-amlodipine-hemi-L-tartrate and S-(−)-amlodipine-hemi-L-tartrate.

The present invention is based on the finding that R-(+)-amlodipine-hemi-L-tartrate-DMAC solvate is almost completely precipitated in as much a volume (ml) of DMAC solvent as 3~10 times the number of grams of (R, S)-amlodipine. For example, when a DMAC solvent is used in a volume of 3~10 ml per g of racemic amlodipine free base, R-(+)-amlodipine-hemi-L-tartrate-DMAC solvate, which is first formed, and a small amount of S-(−)-amlodipine-hemi-L-tartrate-DMAC solvate are formed as precipitates while the remaining large amount of S-(−)-amlodipine-hemi-L-tartrate-DMAC solvate remains more purely dissolved in the solvent.

In accordance with the present invention, L-tartaric acid is used as an optical resolution agent while DMAC serves as a solvent for forming R-(+)-amlodipine-hemi-L-tartrate-DMAC solvate as a precipitate, thereby allowing the S-(−)-amlodipine, remaining soluble therein, to be obtained at high yield to thus achieve a satisfactory enantiomeric excess (e.e).

The method for separating S-(−)-amlodipine from racemic amlodipine in accordance with the present invention may be elucidated as illustrated in the following Reaction Scheme.

[Reaction Scheme 1]

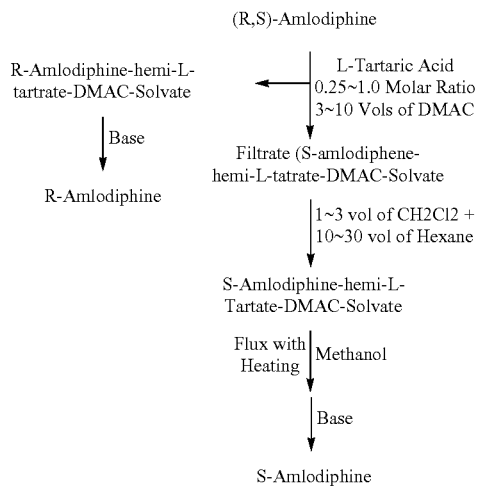

First of all, racemic amlodipine is dissolved in dimethylacetamide (DMAC) and is then reacted with L-tartaric acid to form R-(+)-amlodipine-hemi-L-tartrate-DMAC solvate as a precipitate. In accordance with the present invention, dimethylacetamide (DMAC) is used in a volumetric amount (in ml) as much as 3~10 times the weight (grams) of racemic amlodipine free base, and the L-tartaric acid is used in an amount of 0.25~1.0 mole per mole of racemic amlodipine free base. The resulting precipitate is completely removed through filtration. Then, the remaining DMAC filtrate is mixed with methylene chloride and n-hexane for 12 hrs with stirring to afford S-(−)-amlodipine-hemi-L-tartrate-DMAC solvate as a precipitate. For this, methylene chloride and n-hexane are preferably used in volumetric amounts (ml) 1~3 times and 10~30 times as much as that of racemic amlodipine, respectively. This precipitate is fluxed with heating and filtrated, followed by treatment with a base to produce S-(−)-amlodipine. The treatment with the base is conducted in methylene chloride. Examples of the base useful in the treatment include hydroxides, hydrates, oxides, carbonates, bicarbonates and amides of alkali or alkaline earth metals, with preference for hydroxides of alkali or alkaline earth metals, and particularly preferably for sodium hydroxide.

Over conventional methods, the method according to the present invention has the advantage of requiring a shorter time for crystallization from the filtrate and a far higher production yield.

Featuring the use of inexpensive L-tartaric acid as an optical resolution agent and DMAC as a solvent, the separation method of the present invention allows the resolution of S-(−)-amlodipine from racemic amlodipine at high yield and to a satisfactory enantiomeric excess, and thus is economically favorable and applicable to the mass production of the optical isomer.

In accordance with another aspect thereof, the present invention provides a pharmaceutical composition for the prevention and treatment of cardiovascular diseases, comprising S-(−)-amlodipine as an active ingredient.

In addition to S-(−)-amlodipine, the pharmaceutical composition of the present invention may comprise at least one known active ingredient useful in the prevention or treatment of cardiovascular diseases.

For dosage forms, the pharmaceutical composition of the present invention may be formulated in combination with at least one pharmaceutically acceptable vehicle. Examples of the pharmaceutically acceptable vehicle include saline, sterile water, Ringer's solution, buffered saline, a dextrose solution, a maltodextrin solution, glycerol, ethanol and combinations thereof. If necessary, a conventional additive, such as an antioxidant, a buffer, an anti-bacterial agent, etc., may be added to the composition. Also, the pharmaceutical composition of the present invention may optionally be formulated with a diluent, a surfactant, a binder and/or a lubricant, into an injection, such as an aqueous solution, a suspension, an emulsion, etc., a tablet, a capsule, a granule or a pill. Furthermore, the formulation of the pharmaceutical composition of the present invention may be conducted according to methods known in the art, such as that described in Remington's Pharmaceutical Science (most recent edition), Mack Publishing Company, Easton Pa., depending on the disease and/or ingredients.

The pharmaceutical composition of the present invention may be administered orally or non-orally (e.g., intravenously, subcutaneously, intraperitoneally, or topically) at a dose depending on various factors including the patient's weight, age, gender, state of health, diet, administration route, number of administrations, excretion rate, severity of illness, and the like. The S-(−)-amlodipine may be administered in a single dose or in several doses per day with a daily dose ranging from 0.1 to 20 mg/kg, and preferably from 2.5 to 5.0 mg/kg.

For the prevention or treatment of cardiovascular diseases, the pharmaceutical composition of the present invention may be used alone or in combination with other therapies, including surgical therapy, hormonal therapy, and/or chemical therapy, or a biological response regulator.

A better understanding of the present invention may be obtained through the following examples, which are set forth to illustrate, but are not to be construed as the limit of the present invention.

In the following examples, the optical purity (enantiomeric excess) of the compound was determined by chiral HPLC at a detection wavelength of 360 nm with a mixture of 80:20 disodium hydrogen phosphate (20 mM, pH 7.0):acetonitrile running at a flow rate of 1 ml/min on an ES-OVM Ovomucoid 15 cm column (Ultron).

Advantageous Effects

Featuring the use of inexpensive L-tartaric acid as an optical resolution agent and DMAC as a solvent, the separation method of the present invention allows the resolution of S-(−)-amlodipine from racemic amlodipine at high yield and to a satisfactory enantiomeric excess. Also, the method according to the present invention has the advantage of requiring a shorter time for crystallization from the filtrate and a far higher production yield over conventional methods. Consequently, the method of the present invention is economically favorable and applicable to the mass production of the optical isomer.

BEST MODE FOR CARRYING OUT THE INVENTION

Example 1

Separation of S-(−)-Amlodipine from Racemic Amlodipine

Preparation of S-(−)-amlodipine-hemi-L-tartrate-DMAC solvate from (R,S)-amlodipine 10 g (24.26 mmol) of (R,S)-amlodipine was dissolved in 50 ml of dimethyl-lacetamide (DMAC), to which 3.8 g (1.0 molar equivalents) of L-tartaric acid was then added. The resulting mixture was cooled to 5° C. and stirred for 2 hrs. After the precipitate thus formed was removed through filtration, the remaining filtrate was mixed with 30 ml of methylene chloride and 250 ml of n-hexane for 12 hrs with stirring. The precipitate thus formed was washed with 30 ml of n-hexane and dried at 50° C. in a vacuum to afford S-(−)-amlodipine-hemi-L-tartrate-DMAC solvate.

yield: 5.51 g (40%),
m.p.: 136~140° C.,
chiral HPLC: 98.9% ee,
$^1$H-NMR (CD$_3$OD): 7.39 (d, 1H) 7.25 (d, 1H) 7.10 (t, 1H) 7.08 (t, 1H) 5.41 (s, 1H) 4.77 (d, 1H) 4.69 (d, 1H) 4.36 (s, 1H) 4.05 (m, 2H) 3.78 (t, 2H) 3.58 (s, 3H) 3.22 (m, 2H) 3.05 (s, DMAC) 2.92 (s, DMAC) 2.34 (s, 3H) 2.08 (s, DMAC) 1.16 (t, 3H).

2. Preparation of S-(−)-amlodipine from S-(−)-amlodipine-hemi-L-tartrate-DMAC solvate To 100 ml of methanol was added 5.5 g of the S-(−)-amlodipine-hemi-L-tartrate-DMAC solvate obtained in step 1, followed by refluxing for 6 hrs with heating. After cooling to room temperature and filtration, the precipitate thus obtained was dissolved in 33 ml of methylene chloride and then treated with 33 ml of 2N NaOH for 40 min with stirring. An organic layer formed by layer separation was washed with distilled water and concentrated. To the oil phase were slowly added 5 ml of methylene chloride and 50 ml of n-hexane, followed by stirring for 4 hrs. The precipitate thus formed was removed by filtration, washed with 30 ml of n-hexane, and dried at 50° C. in a vacuum to give S-(−)-amlodipine.

yield: 3.74 g (95%),
m.p.: 108-110° C.,
chiral HPLC: 99% ee,
$^1$H-NMR (CD$_3$OD): 7.40 (d, 1H) 7.36 (d, 1H) 7.24 (t, 1H) 7.09 (m, 1H) 5.40 (s, 1H) 4.72 (d, 1H) 4.59 (d, 1H) 4.03 (m, 2H) 3.57 (s, 3H) 2.88 (t, 2H) 2.32 (s, 3H) 1.14 (t, 3H).

The invention claimed is:

1. A method for separation of S-(−)-amlodipine from a racemic amlodipine, comprising:
   1) reacting an amlodipine racemate with L-tartaric acid in a dimethylacetamide (DMAC) solvent and filtering off a precipitate [R-(+)-amlodipine-hemi-L-tartrate-DMAC solvate],
   2) adding methylene chloride and n-hexane to filtrate remaining from step 1) to afford an S-(−)-amlodipine-hemi-L-tartrate-DMAC solvate, and
   3) purifying the S-(−)-amlodipine-hemi-L-tartrate-DMAC solvate with methanol, followed by treatment with a base,
   wherein the methylene chloride and n-hexane in step 2) are used in volumetric amounts (mL) 1 to 3 and 10 to 30 times as much as weight (g) of the racemic amlodipine, respectively.

2. The method according to claim 1, wherein the dimethylacetamide (DMAC) solvent is used in a volumetric amount (ml) 3 to 10 times as much as a weight (grams) of the racemic amlodipine.

3. The method according to claim 1, wherein the L-tartaric acid is used in an amount of 0.25~1.0 mole per mole of racemic amlodipine.

4. The method according to claim 1, wherein the base of step 3 is selected from a group consisting of hydroxides, hydrates, oxides, carbonates, bicarbonates and amides of alkali metals or alkaline earth metals.

5. The method according to claim 4, wherein the base is a hydroxide of alkali metal or alkaline earth metal.

6. The method according to claim 5, wherein the base is sodium hydroxide.

* * * * *